United States Patent
Wohlman et al.

(10) Patent No.: US 7,056,350 B1
(45) Date of Patent: Jun. 6, 2006

(54) PROCESS AND COMPOSITION FOR DYEING HAIR UTILIZING CATIONIC MEADOWFOAM CONDITIONING AGENTS

(75) Inventors: Alan Wohlman, Chicago, IL (US);
Apolonio L. Villanueva, Northbrook, IL (US); Anthony J. O'Lenick, Jr., Dacula, GA (US)

(73) Assignee: FanTech Corporation, Chicago, IL (US)

( * ) Notice: Subject to any disclaimer, the term of this patent is extended or adjusted under 35 U.S.C. 154(b) by 381 days.

(21) Appl. No.: 10/429,595

(22) Filed: May 6, 2003

(51) Int. Cl.
*A61K 7/13* (2006.01)

(52) U.S. Cl. .................... 8/405; 8/406; 8/408; 8/410; 8/411; 8/421; 8/606; 132/202; 132/208; 424/70.11; 424/70.122; 424/70.17

(58) Field of Classification Search ............... 8/405, 8/406, 408, 410, 411, 421, 606; 132/202, 132/208; 424/70.11, 70.122, 70.17
See application file for complete search history.

(56) References Cited

U.S. PATENT DOCUMENTS 6,383,232 B1 * 5/2002 Wohlman et al. ............ 8/408

* cited by examiner

*Primary Examiner*—Eisa Elhilo

(57) ABSTRACT

The present invention relates to a composition, process for preparation and use of a novel hair dyeing composition in the personal care industry. The composition when used in the dyeing process for hair results in a permanent coloration to the hair and improves manageability of the hair and minimizes damage from dyeing process. The use of a cationic compound based upon meadowfoam seed oil provides unexpected penetration of the hair by the dye, unexpected oxidative stability in the dye compositions, and unexpected color deposition to the hair.

16 Claims, No Drawings

PROCESS AND COMPOSITION FOR DYEING HAIR UTILIZING CATIONIC MEADOWFOAM CONDITIONING AGENTS

DESCRIPTION OF THE ART AND PRACTICES

The coloring of hair is one of the most important acts of adornment since the origin of man. The most effective coloring preparations on the market today are oxidative dyes. Almost all hair coloring is now performed with oxidation dye, both in the beauty salon and in homes. This type of dye dominates the market because the processes using these materials are quick, and lasting. These materials are called oxidative dyes because the dye must be placed on the hair, penetrate it and be oxidized, most commonly with hydrogen peroxide to make a color.

The dye when applied to the hair must be of low enough molecular weight to penetrate the hair, and be capable of being polymerized in the hair, in the presence of base and hydrogen peroxide, to form larger molecular weight colors. The chemical polymerization in the presence of base and peroxide is a coupling or condensation reaction. The base is an alkaline material selected from the group consisting of sodium hydroxide, potassium hydroxide, calcium hydroxide or the like. The base swells the hair and makes the penetration by the dye more rapid. It also participates in the condensation reaction.

The use of alkaline materials and hydrogen peroxide on the hair has a damaging effect upon the hair. Resulting in physical and chemical damage. However these additives have been necessary to (a) open up the hair to make the penetration of the dye more effective and (b) to condense the dyes.

It is highly desirable to be able to deliver the dye to the hair and facilitate the penetration of the dye into the hair. We have surprisingly found that cationic compounds based upon meadowfoam seed oil allow for the efficient and through conditioning of the hair while the dyeing process is carried out, providing outstanding softness to treated hair without interfering with the deposition of the color.

THE INVENTION

SUMMARY OF THE INVENTION

The present invention relates to a composition, process for preparation and use of a novel hair dyeing composition in the personal care industry. The composition when used in the dyeing process for hair results in a permanent coloration to the hair and improves softness, texture, and manageability of the hair and minimizes damage from dyeing process.

The use of cationic compounds, based upon meadowfoam seed oil, co-applied during the dyeing process, provides unexpected conditioning of the hair. The improved functionality of this specific cationic compound is based upon this oil relates to the unique structure of the meadowfoam seed oil. The fatty distribution of the oil ranges from 20 to 22 carbons and has unsaturation in specific locations. The oil contains 97% by weight higher unsaturated alkyl groups. Typically, meadowfoam oil contains 60–65% of a twenty carbon mono-carboxy acid having one unsaturation between carbon 5 and 6. Additionally, it contains 12–20% of a twenty two carbon mono-carboxy acid having one unsaturation between either carbon 5 and 6, or carbon 13 and 14 and 15–28% of a twenty two carbon mono-carboxy acid having one unsaturation between both carbon 5 and 6, or carbon 13 and 14. The combination of the fact that there are 20 to 22 carbon atoms in the group leads to lack of volatility, the presence of unsaturation leads to liquidity and the fact that the di-unsaturated moieties are not conjugated leads to outstanding oxidative stability.

Meadowfoam seed oil is a triglyceride that conforms to the following structure:

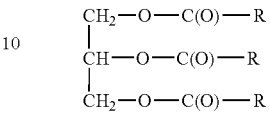

Wherein R is:
60–65% by weight —$(CH_2)_3$—CH=CH—$(CH_2)_{13}$—$CH_3$
12–20% by weight a mixture of —$(CH_2)_3$—CH=CH—$(CH_2)_{15}$—$CH_3$ and
—$(CH_2)_{11}$—CH=CH—$(CH_2)_7$—$CH_3$ and
and
15–28% by weight
—$(CH_2)_3$—CH=CH—$(CH_2)_6$—CH=CH—$(CH_2)_6$—$CH_3$.

OBJECT OF THE INVENTION

It is the objective of the present invention to provide a composition which contains (a) a cationic meadowfoam seed oil derived compound, (b) hair dye colors including main oxidation bases and coupling agents, (c) an oxidizing agent, and (d) a base selected from the group consisting of ammonia, NaOH and KOH. The composition is mixed together just prior to use and provides a very efficient dyeing process for hair. The ease of penetration, overall uniformity of color deposition and overall condition of the hair so treated is outstanding and here to fore unattainable using older technology.

DETAILED DESCRIPTION OF THE INVENTION

The compositions of the present invention are made up of the following components:
(c) a cationic compound conforming to the following structure:

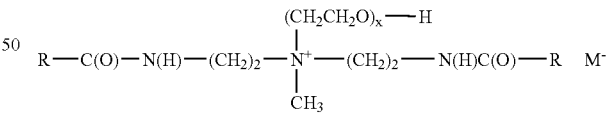

wherein:
R is derived from meadowfoam seed oil and has the following composition;
60–65% by weight —$(CH_2)_3$—CH=CH—$(CH_2)_{13}$—$CH_3$
12–20% by weight a mixture of
—$(CH_2)_3$—CH=CH—$(CH_2)_{15}$—$CH_3$ and
—$(CH_2)_{11}$—CH=CH—$(CH_2)_7$—$CH_3$ and
15–28% by weight
—$(CH_2)_3$—CH=CH—$(CH_2)_6$—CH=CH—$(CH_2)_6$—$CH_3$;
x is 2;
M is $SO_4CH_3$ (d) hair dye colors including main oxidation bases and coupling agents selected from the group consisting of;
p-phenylenediamine,
p-aminophenol hydrochloride,
2-amino-4-nitrophenol,
4-nitro-o-phenylenediamine,
o-aminophenol,
resorcinol,
pryogallol,
hydroquinone,
2-4-diaminophenol,
p-aminophenylene base,
2-nitro-o-phenylenediamine,
4,4-diaminoanisole sulfate,
4-nitro-o-phenyenediamine,
p-amiophenol,
p-toluylenediamine hydrochloride,
m-aminophenol,
2,6-diaminopyridine,
6-chloro-4-nitro-2-aminophenol;
(f) an oxidizing agent namely hydrogen peroxide
(g) a base selected from the group consisting of ammonia, NaOH, and KOH. and
(h) water.

The compositions of the present invention are used in a process for the dyeing of hair, which comprises contacting the hair with an effective dyeing concentration of a composition, which comprises:

In a preferred embodiment the composition comprises;
(f) between 0.5% to 10.0% by weight of a cationic compounds having the following structure:

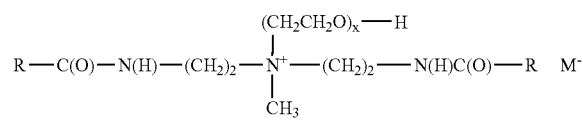

wherein:
R is derived from meadowfoam seed oil, comprising
60–65% by weight —$(CH_2)_3$—CH=CH—$(CH_2)_{13}$—$CH_3$
12–20% by weight a mixture of
—$(CH_2)_3$—CH=CH—$(CH_2)_{15}$—$CH_3$ and
—$(CH_2)_{11}$—CH=CH—$(CH_2)_7$—$CH_3$ and
and
15–28% by weight
—$(CH_2)_3$—CH=CH—$(CH_2)_6$—CH=CH—$(CH_2)_6$—$CH_3$;
x is 2;
M is $SO_4CH_3$;
(g) between 1.0% and 10.0% by weight of a hair dye color including main oxidation bases and coupling agents selected from the group consisting of;
p-phenylenediamine,
p-aminophenol hydrochloride,
2-amino-4-nitrophenol,
4-nitro-o-phenylenediamine,
o-aminophenol,
resorcinol,
pryogallol,
hydroquinone,
2-4-diaminophenol,
p-aminophenylene base,
2-nitro-o-phenylenediamine,
4,4-diaminoanisole sulfate,
4-nitro-o-phenyenediamine,
p-amiophenol,
p-toluylenediamine hydrochloride,
m-aminophenol,
2,6-diaminopyridine,
6-chloro-4-nitro-2-aminophenol;
(h) between 1.0% and 15% by weight of an oxidizing agent, namely hydrogen peroxide;
(i) between 0.5 and 10% by weight of a base selected from the group consisting of ammonia, NaOH, and KOH. and
(e) between 97.5% and 60.0% by weight water.

The compositions of the present invention are used in a process for the dyeing of hair, which comprises contacting the hair with an effective dyeing concentration of a composition, which comprises:

EXAMPLES

A. Cationic Compounds

Example 1

This compound is commercially available from The Fanning Corporation.

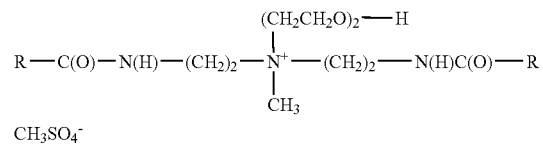

$CH_3SO_4^-$

R is derived from meadowfoam seed oil and has the following composition;
60–65% by weight —$(CH_2)_3$—CH=CH—$(CH_2)_{13}$—$CH_3$
12–20% by weight a mixture of
—$(CH_2)_3$—CH=CH—$(CH_2)_{15}$—$CH_3$ and
—$(CH_2)_{11}$—CH=CH—$(CH_2)_7$—$CH_3$ and
15–28% by weight
—$(CH_2)_3$—CH=CH—$(CH_2)_6$—CH=CH—$(CH_2)_6$—$CH_3$.

Example 2

This compound is commercially available from The Fanning Corporation.

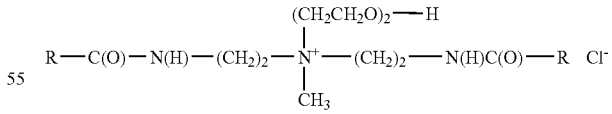

R is derived from meadowfoam seed oil and has the following composition;
60–65% by weight —$(CH_2)_3$—CH=CH—$(CH_2)_{13}$—$CH_3$
12–20% by weight a mixture of
—$(CH_2)_3$—CH=CH—$(CH_2)_{15}$—$CH_3$ and
—$(CH_2)_{11}$—CH=CH—$(CH_2)_7$—$CH_3$ and
15–28% by weight
—$(CH_2)_3$—CH=CH—$(CH_2)_6$—CH=CH—$(CH_2)_6$—$CH_3$.

Example 3

This compound is commercially available from The Fanning Corporation.

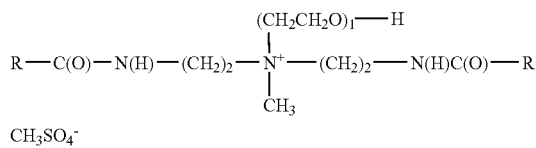

CH$_3$SO$_4^-$

R is derived from meadowfoam seed oil and has the following composition;
60–65% by weight —(CH$_2$)$_3$—CH=CH—(CH$_2$)$_{13}$—CH$_3$
12–20% by weight a mixture of
—(CH$_2$)$_3$—CH=CH—(CH$_2$)$_{15}$—CH$_3$ and
—(CH$_2$)$_{11}$—CH=CH—(CH$_2$)$_7$—CH$_3$ and
15–28% by weight
—(CH$_2$)$_3$—CH=CH—(CH$_2$)$_6$—CH=CH—(CH$_2$)$_6$—CH$_3$.

Example 4

This compound is commercially available from The Fanning Corporation.

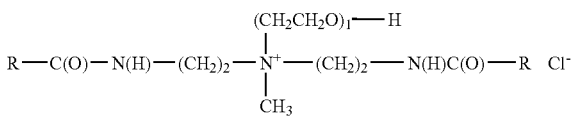

R is derived from meadowfoam seed oil and has the following composition;
60–65% by weight —(CH$_2$)$_3$—CH=CH—(CH$_2$)$_{13}$—CH$_3$
12–20% by weight a mixture of
—(CH$_2$)$_3$—CH=CH—(CH$_2$)$_{15}$—CH$_3$ and
—(CH$_2$)$_{11}$—CH=CH—(CH$_2$)$_7$—CH$_3$ and
15–28% by weight
—(CH$_2$)$_3$—CH=CH—(CH$_2$)$_6$—CH=CH—(CH$_2$)$_6$—CH$_3$.

Examples 5–22

Hair Dye Colors Including Main Oxidation Bases and Coupling Agents

| Example | Compound |
|---|---|
| 5. | p-phenylenediamine, |
| 6. | p-aminophenol hydrochloride, |
| 7. | 2-amino-4-nitrophenol, |
| 8. | 4-nitro-o-phenylenediamine, |
| 9. | o-aminophenol, |
| 10. | resorcinol, |
| 11. | pryogallol, |
| 12. | hydroquinone, |
| 13. | 2-4-diaminophenol, |
| 14. | p-aminophenylene base, |
| 15. | 2-nitro-o-phenylenediamine, |
| 16. | 4,4-diaminoanisole sulfate, |
| 17. | 4-nitro-o-phenyenediamine, |
| 18. | p-amiophenol, |
| 19. | p-toluylenediamine hydrochloride, |
| 20. | m-aminophenol, |
| 21. | 2,6-diaminopyridine, |
| 22. | 6-chloro-4-nitro-2-aminophenol; |

Example 23

Oxidizing Agent

Example 23 H$_2$O$_2$ (35% in aqueous solution);

Example 24–26

Base

Example 24 ammonia 28% in aqueous solution
Example 25 NaOH 50% in aqueous solution,
Example 26 KOH 45% in aqueous solution.

Formulations

Typical formulations used commercially contain a variety of ingredients. Addition of the compounds of the present invention to the formulated products just prior to application results in many desirable properties.

Standard Formulation—(No Additive)

| Formulation #1 Red Component | % wt |
|---|---|
| WATER | 54.5 |
| OLEIC ACID | 4.0 |
| C12–15 PARETH-3 | 4.0 |
| AMMONIUM HYDROXIDE | 5.0 |
| BEHENTRIMONIUM CHLORIDE | 4.0 |
| C11–15 PARETH-9 | 4.0 |
| FRAGRANCE | 1.0 |
| STEARETH-21 | 3.0 |
| PROPYLENE GLYCOL | 1.0 |
| CETYL ALCOHOL | 3.0 |
| POLYQUATERNIUM-47 | 2.0 |
| PEG-150/STEARYL COPOLYMER | 1.0 |
| STEARYL ALCOHOL | 1.0 |
| ERYTHORBIC ACID | 0.5 |
| EDTA | 0.1 |
| SODIUM SULFITE | 0.1 |
| SODIUM METASILICATE | 0.1 |
| 4-AMINO-2-HYDROXYTOLULENE | 1.0 |
| P-AMINOPHENOL | 1.0 |
| MICA | 0.5 |
| IRON OXIDES | 0.1 |
| 1-NAPHTHOL | 1.0 |
| P-PHENYLENEDIAMINE | |
| TITANIUM DIOXIDE | 0.1 |
| 35% HYDROGEN PEROXIDE | 12.0 |
| Total | 100.0 |

Formulation of the Current Invention

| Formulation #2 Red Component | % wt |
|---|---|
| WATER | 48.5 |
| OLEIC ACID | 4.0 |
| C12–15 PARETH-3 | 4.0 |
| AMMONIUM HYDROXIDE | 5.0 |
| BEHENTRIMONIUM CHLORIDE | 4.0 |
| C11–15 PARETH-9 | 4.0 |
| FRAGRANCE | 1.0 |
| STEARETH-21 | 3.0 |
| PROPYLENE GLYCOL | 1.0 |
| CETYL ALCOHOL | 3.0 |
| POLYQUATERNIUM-47 | 2.0 |
| PEG-150/STEARYL COPOLYMER | 1.0 |
| STEARYL ALCOHOL | 1.0 |
| ERYTHORBIC ACID | 0.5 |
| EDTA | 0.1 |
| SODIUM SULFITE | 0.1 |
| SODIUM METASILICATE | 0.1 |
| 4-AMINO-2-HYDROXYTOLULENE | 1.0 |
| P-AMINOPHENOL | 1.0 |
| MICA | 0.5 |
| IRON OXIDES | 0.1 |
| 1-NAPHTHOL P-PHENYLENEDIAMINE | 1.0 |
| TITANIUM DIOXIDE | 0.1 |
| Example 4 | 6.0 |
| 35% HYDROGEN PEROXIDE | 12.0 |
| Total | 100.0 |

Formulation of the Current Invention

| Formulation #3 Red Component | % wt |
|---|---|
| WATER | 48.5 |
| OLEIC ACID | 4.0 |
| C12–15 PARETH-3 | 4.0 |
| AMMONIUM HYDROXIDE | 5.0 |
| BEHENTRIMONIUM CHLORIDE | 4.0 |
| C11–15 PARETH-9 | 4.0 |
| FRAGRANCE | 1.0 |
| STEARETH-21 | 3.0 |
| PROPYLENE GLYCOL | 1.0 |
| CETYL ALCOHOL | 3.0 |
| POLYQUATERNIUM-47 | 2.0 |
| PEG-150/STEARYL COPOLYMER | 1.0 |
| STEARYL ALCOHOL | 1.0 |
| ERYTHORBIC ACID | 0.5 |
| EDTA | 0.1 |
| SODIUM SULFITE | 0.1 |
| SODIUM METASILICATE | 0.1 |
| 4-AMINO-2-HYDROXYTOLULENE | 1.0 |
| P-AMINOPHENOL | 1.0 |
| MICA | 0.5 |
| IRON OXIDES | 0.1 |
| 1-NAPHTHOL P-PHENYLENEDIAMINE | 1.0 |
| TITANIUM DIOXIDE | 0.1 |
| Example 2 | 6.0 |
| 35% HYDROGEN PEROXIDE | 12.0 |

A scale of 1–5 was used to evaluate the various attributes of hair treated with a commercial formulation of hair dye and one using the same hair dye to which was added the silicone ester prior to use. (process of the present invention). 1 was defined as poor and 5 defined as excellent.

| Attribute | Standard Formulation Formulation 1 | Present Invention Formulation 2 | Present Invention Formulation 3 |
|---|---|---|---|
| Formulation Stability | 5 | 5 | 5 |
| Softness of hair | 3 | 5 | 5 |
| Color Intensity | 3 | 5 | 5 |

What is claimed:

1. A process for the simultaneous conditioning and dyeing of hair that comprises contacting the hair with an effective conditioning concentration of a composition that comprises:
   (a) a cationic compound conforming to the following structure:

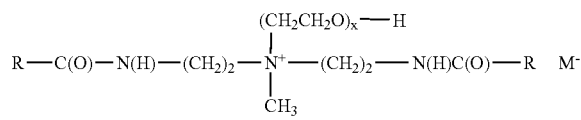

wherein:
R is derived from meadowfoam seed oil and has the following composition;
60–65% by weight —$(CH_2)_3$—CH=CH—$(CH_2)_{13}$—$CH_3$
12–20% by weight a mixture of
—$(CH_2)_3$—CH=CH—$(CH_2)_{15}$—$CH_3$ and
—$(CH_2)_{11}$—CH=CH—$(CH_2)_7$—$CH_3$
x is 2;
M is $SO_4CH_3$;
and
   (b) hair dye colors including main oxidation bases and coupling agents selected from the group consisting of;
   p-phenylenediamine,
   p-aminophenol hydrochloride,
   2-amino-4-nitrophenol,
   4-nitro-o-phenylenediamine,
   o-aminophenol,
   resorcinol,
   pryogallol,
   hydroquinone,
   2-4-diaminophenol,
   p-aminophenylene base,
   2-nitro-o-phenylenediamine,
   4,4-diaminoanisole sulfate,
   4-nitro-o-phenyenediamine,
   p-amiophenol,
   p-toluylenediamine hydrochloride,
   m-aminophenol,
   2,6-diaminopyridine,
   6-chloro-4-nitro-2-aminophenol;
   (c) an oxidizing agent, most commonly hydrogen peroxide
   (d) a base selected from the group consisting of ammonia, NaOH, and KOH; and
   (e) water.

2. A process for the simultaneous conditioning and dyeing of hair that comprises contacting the hair with an effective conditioning concentration of a composition that comprises:

(a) between 0.1 and 10.0% by weight a cationic compound conforming to following structure:

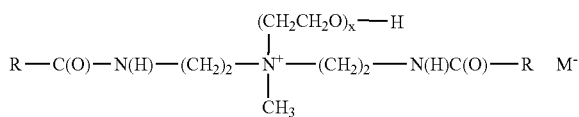

wherein:
R is derived from meadowfoam seed oil and has the following composition;
60–65% by weight $-(CH_2)_3-CH=CH-(CH_2)_{13}-CH_3$
12–20% by weight a mixture of
$-(CH_2)_3-CH=CH-(CH_2)_{15}-CH_3$ and
$-(CH_2)_{11}-CH=CH-(CH_2)_7-CH_3$
x is 2;
M is $SO_4CH_3$;
and
(b) between 1.0% and 10.0% by weight hair dye colors including main oxidation bases and coupling agents selected from the group consisting of;
p-phenylenediamine,
p-aminophenol hydrochloride,
2-amino-4-nitrophenol,
4-nitro-o-phenylenediamine,
o-aminophenol,
resorcinol,
pryogallol,
hydroquinone,
2-4-diaminophenol,
p-aminophenylene base,
2-nitro-o-phenylenediamine,
4,4-diaminoanisole sulfate,
4-nitro-o-phenyenediamine,
p-amiophenol,
p-toluylenediamine hydrochloride,
m-aminophenol,
2,6-diaminopyridine,
6-chloro-4-nitro-2-aminophenol;
(c) between 1.0% and 15% by weight of hydrogen peroxide;
(d) between 0.5% and 10% by weight of a base selected from the group consisting of ammonia, NaOH, and KOH; and
(e) between 97.5% and 60.0% by weight water.

3. A process of claim 1 wherein said hair dye colors is o-aminophenol.

4. A process of claim 1 wherein said hair dye colors is resorcinol.

5. A process of claim 1 wherein said hair dye colors is pryogallol.

6. A process of claim 1 wherein said hair dye colors is hydroquinone.

7. A process of claim 1 wherein said hair dye colors is 4-nitro-o-phenylenediamine.

8. A process of claim 1 wherein said hair dye colors is 2-amino-4-nitrophenol.

9. A process of claim 1 wherein said hair dye colors is p-aminophenol hydrochloride.

10. A process of claim 1 wherein said hair dye colors is p-phenylenediamine.

11. A process of claim 1 wherein said hair dye colors is 2-4-diaminophenol.

12. A process of claim 1 wherein said hair dye colors is p-aminophenylene base.

13. A process of claim 1 wherein said hair dye colors is 2-nitro-o-phenylenediamine.

14. A process of claim 1 wherein said hair dye colors is 4,4-diaminoanisole sulfate.

15. A process of claim 1 wherein said hair dye colors is 4-nitro-o-phenyenediamine.

16. A process of claim 1 wherein said hair dye colors is p-amiophenol.

* * * * *